United States Patent [19]

Patel

[11] Patent Number: 4,468,527

[45] Date of Patent: Aug. 28, 1984

[54] FLUORINATED ALCOHOLS

[75] Inventor: Kalyanji U. Patel, St. Paul, Minn.

[73] Assignee: Minnesota Mining and Manufacturing Company, St. Paul, Minn.

[21] Appl. No.: 358,335

[22] Filed: Mar. 15, 1982

Related U.S. Application Data

[60] Division of Ser. No. 214,324, Dec. 8, 1980, Pat. No. 4,340,749, which is a division of Ser. No. 101,515, Dec. 21, 1979, Pat. No. 4,264,484, which is a continuation-in-part of Ser. No. 6,252, Jan. 24, 1979, abandoned.

[51] Int. Cl.$^3$ .................. C07C 143/76; C07C 43/12; C07C 31/34
[52] U.S. Cl. .................. 564/96; 564/209; 568/677; 568/615; 568/32; 568/416; 568/607; 568/662; 568/812; 568/844
[58] Field of Search .............. 568/677, 615, 32, 416, 568/607, 662, 812, 844; 564/96, 209

[56] References Cited

U.S. PATENT DOCUMENTS 3,663,604  5/1972  Blochi .................... 568/677 X
4,289,892  9/1981  Soch ...................... 568/615 X

FOREIGN PATENT DOCUMENTS 1172082  11/1969  United Kingdom ............ 568/615
1410845  10/1975  United Kingdom .

*Primary Examiner*—Bernard Helfin
*Attorney, Agent, or Firm*—Cruzan Alexander; Donald M. Sell; William G. Ewert

[57] ABSTRACT

A fluoroaliphatic radical- and aliphatic chlorine-containing alcohol containing more than 25 weight percent carbon-bonded fluorine in the form of fluoroaliphatic radicals and at least one aliphatic chlorine, an ester of said alcohol and a carboxycylic acid being useful in the treatment of carpet.

3 Claims, No Drawings

FLUORINATED ALCOHOLS

This is a division of application Ser. No. 214,324, filed Dec. 8, 1980 and now U.S. Pat. No. 4,340,749, which is a divisional of Ser. No. 101,515, filed Dec. 21, 1979 (now U.S. Pat. No. 4,264,484) which is a continuation-in-part of Ser. No. 6,252, filed Jan. 24, 1979 (now abandoned).

This invention relates to a carpet treatment with fluorochemical compositions and to the carpet so treated. In another aspect, it relates to such fluorochemical compositions and to their preparation.

In the industrial production of carpet it is common now to treat the pile of the carpet with a composition to impart added desirable properties thereto, such as oil and water repellancy and resistance to soiling by particulate or dry soil. Fluorochemical compositions are commercially used for this purpose and various patents disclose a variety of such compositions, e.g., U.S. Pat. Nos. 3,923,715 (Dettre et al), 4,043,923 (Ludas), 4,043,964 (Sherman et al), and 3,816,167 (Schultz et al).

The fluorochemical carpet treatment is generally the last in a series of operations in the manufacture of carpet, many of which operations (for example, space dyeing and stock dyeing) entail applying to the carpet a host of processing aids, such as lubricants, release agents, print paste thickeners, and leveling agents. Such processing aids are particularly required in the manufacture of carpets of synthetic fibers, the bulk of present day carpeting. Small amounts of the processing aids often remain on the carpet face pile and act as contaminants which interfere with the fluorochemical treatment and diminish or prevent the desired result thereof. This unsatisfactory situation arises particularly in the case of the fluorochemical treatments which entail a relatively moderate heat curing step, e.g., treatments at below about 130° C. and sometimes less than 100° C. High curing temperatures, though oftentimes conducive to a satisfactory treatment, are costly, and thus undesirable, and at times are harmful to the particular carpet construction. Thus, while many currently used fluorochemical compositions have demonstrated utility in providing the carpet with stain repellancy and soil resistance, unfortunately a significant amount of the carpet manufactured, e.g. 30%, can not be treated to obtain the desired properties, especially stain repellancy, e.g. water and oil repellancy.

It is difficult in the operation of a carpet mill to predict which of the carpet lines are going to present problems in obtaining satisfactory fluorochemical finishing. Thus, there is a need for a treatment which results in the desired properties equally well on "clean" as well as "contaminated" carpet and with no more expense than that incurred by currently used fluorochemical treatments. The present invention satisfies such need by providing novel fluorochemical compositions.

The fluorochemical compositions useful in the carpet treatment process of this invention comprise fluoroaliphatic radical- and aliphatic chlorine-containing esters. One class of these esters can be prepared by reacting precursor fluoroaliphatic radical- and chlorine-containing alcohols (which are themselves novel) with an organic acid such as a mono- or polycarboxylic acid, especially citric acid, to prepare the corresponding simple ester, e.g. citrate. Another class can be prepared by reacting said alcohols, or said simple esters if they contain an isocyanate-reactive hydrogen atom (as in the case of citrates), with isocyanates, such as 2,4-tolylene diisocyanate and isophrone diisocyanate, to form isocyanate derivatives, e.g. urethanes (carbamic acid esters).

The fluoroaliphatic radical- and chlorine-containing esters are compounds which are preferably free of anionic groups and are non-ionic or cationic, and thus are compatible with cationic surfactants and can be used in carpet treating compositions which are in the form of an aqueous emulsion, suspension or dispersion containing such surfactants, e.g. fluoroaliphatic surfactants such as $C_8F_{17}SO_2NHC_3H_6N^+(CH_3)_3Cl^-$.

The fluoroaliphatic radical ($R_f$) is a fluorinated, preferably saturated, monovalent, non-aromatic, aliphatic radical of at least three fully fluorinated carbon atoms. The chain may be straight, branched, or, if sufficiently large, cyclic, and may be interrupted by divalent oxygen atoms or trivalent nitrogen atoms bonded only to carbon atoms. A fully fluorinated group is preferred, but hydrogen or chlorine atoms may be present as substituents in the fluorinated aliphatic radical provided that not more than one atom of either is present in the radical for every two carbon atoms, and that the radical must at least contain a terminal perfluoromethyl group. Preferably, the fluorinated aliphatic radical contains not more than 20 carbon atoms because such a large radical results in inefficient use of the fluorine content.

The term "aliphatic chlorine" refers to a chlorine atom bonded to a carbon atom whose other valences are satisfied by three other atoms, one of which is carbon and the other two are carbon or hydrogen.

The fluoroaliphatic radical- and chlorine-containing esters have at least one major transition, viz., a glass transition temperature, $T_g$, or melting point, $T_m$, greater than 25° C., preferably greater than about 40° C. and even more preferably greater than about 45° C. Said esters preferably contain at least 25 weight percent fluorine in the form of said fluoroaliphatic radical and contain at least one aliphatic chlorine atom per molecule.

The precursor fluoroaliphatic radical- and chlorine-containing alcohols (used to make the esters) can be prepared, for example, by reaction of fluoroaliphatic radical-containing epoxide with hydrogen chloride to produce the corresponding fluoroaliphatic radical- and chlorine- containing alcohol. These alcohols must contain more than 25 wt. % of carbon-bonded fluorine, in the form of fluoroaliphatic radical, and at least one aliphatic chlorine. A preferred class of such alcohols can be represented by

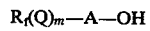
$$R_f(Q)_m-A-OH \qquad I$$

where
- $R_f$ is a fluoroaliphatic radical,
- Q is a divalent linking group free of epoxy-reactive and isocyanate-reactive groups, e.g. —CO—, —CONR—, —SO$_2$NR—, —SO$_2$—, —C$_n$H$_{2n}$—, —C$_6$H$_4$—, —C$_6$H$_2$Cl—, —OC$_2$H$_4$—, or combinations thereof,
- R is H or lower alkyl containing 1-6 carbons, and
- n is 1 to 20,
- m is zero or 1, and
- A is a divalent organic moiety having 2 to 30 carbon atoms, containing at least one aliphatic chlorine atom, and free of hydroxyl-reactive substituents.

An exemplification of the preparation of said alcohols is set forth in Example 1, infra.

The epoxides used in the preparation of the above alcohols can have 1 or more fluoroaliphatic radicals, $R_f$, and 1 or more epoxide or oxirane rings. Readily available epoxides are those corresponding to the formula $$R_f(Q)_m CHCHR \quad \text{II}$$
$$\diagdown O \diagup$$

where
$R_f$ is a fluoroaliphatic radical as described above
Q is a divalent linking group free of epoxy-reactive and isocyanate-reactive groups as described above,
m is zero or 1,
and where the epoxide contains at least about 25 wt. % carbon-bonded fluorine in the form of said fluoroaliphatic radical.

(The terms "free of epoxy-reactive and isocyanate-reactive groups" means the absence of groups which would react with epoxides and isocyanates under the usual reaction conditions, e.g. below about 50° C.)

When the epoxides of formula II are reacted with hydrogen chloride, the resultant alcohols correspond to those of the formula $$R_f(Q)_m CH(OH)CHRCl \quad \text{III}$$

where $R_f$, Q, R, and m are as defined above.

Another method of preparing the alcohol precursors is by reaction of epichlorohydrin with a fluoroaliphatic radical-containing alcohol. Readily available alcohols which can be used in this preparation are those corresponding to the formula $$R_f(Q)_m \overset{R_1}{\underset{R_2}{\overset{|}{C}}}-OH \quad \text{IV}$$

where
$R_f$, Q and m are as defined above,
$R_1$ is hydrogen or a lower alkyl, and
$R_2$ is hydrogen, lower alkyl, or aryl of 6 to 12 carbons and $R_1$ and $R_2$ can be connected together to form a cyclic structure, aromatic or cycloaliphatic, including the hydroxyl-bearing carbon atom shown in formula IV. When the fluoroaliphatic radical-containing alcohols are reacted with epichlorohydrin to form the corresponding fluoroaliphatic alcohols, the latter can correspond to the formula $$R_f(Q)_m\overset{R_1}{\underset{R_2}{\overset{|}{C}}}\left[-OCH_2-\underset{CH_2Cl}{\overset{|}{CH}}-\right]_p OH \quad \text{V}$$

where $R_f$, Q, $R_1$, and $R_2$ are as defined above and p is a small integer, e.g. 1 to 5.

Representative species of fluoroaliphatic compounds containing epoxy-reactive hydrogen atoms which can be used to make the corresponding fluoroaliphatic radical- and chlorine-containing alcohols are those disclosed, for example, in columns 3 and 4 of U.S. Pat. No. 4,043,923 (Loudas) and pages 11 and 12 of copending U.S. application Ser. No. 20133 (Soch).

The aforementioned simple esters can be prepared by conventional esterification techniques from the fluoroaliphatic radical- and chlorine-containing alcohols with mono- or polycarboxcylic acids, e.g. citric acid, malic acid, and trimesic acid; U.S. Pat. No. 3,923,715 (Dettre et al) discloses such esterification techniques. One preferred class of the citrates of this invention can be represented by the formula $$\begin{array}{l}CH_2COO-A-(Q)_m-R_f \\ | \\ HO-CCOO-A-(Q)_m-R_f \\ | \\ CH_2COO-A-(Q)_m-R_f\end{array} \quad \text{VI}$$

where $R_f$, Q and m are as defined above and A is a divalent organic moiety having 2 to 30 carbon atoms and containing at least one aliphatic chlorine atom, said citrates preferably containing at least 25 wt. % carbon-bonded fluorine in the form of $R_f$. Species of citrates within the scope of formula VI are those of the formula:

$$\begin{array}{l}\quad\quad\quad CH_2Cl \\ \quad\quad\quad | \\ CH_2COOCHCH_2N(CH_3)SO_2C_8F_{17} \\ | \\ HO-CCOOCHCH_2N(CH_3)SO_2C_8F_{17} \\ | \quad\quad | \\ \quad\quad CH_2Cl \\ | \\ CH_2COOCHCH_2N(CH_3)SO_2C_8F_{17} \\ | \\ CH_2Cl\end{array} \quad \text{VII}$$

The fluoroaliphatic radical- and chlorine-containing urethanes (or carbamates) of this invention can be prepared by conventional urethane bond-forming reactions disclosed in said U.S. Pat. No. 3,923,715 and "Polyurethanes: Chemistry and Technology", by Saunders and Frisch, Interscience Pub. 1962. Most readily, the urethanes are prepared by reaction of said fluoroaliphatic radical- and chlorine-containing alcohols or those of said simple esters (e.g., citrates) containing an isocyanate-reactive hydrogen atom with an isocyanate-containing compound, such as 2,4-tolylene diisocyanate. Other aromatic, aliphatic, or alicyclic isocyanates can be substituted for tolylene diisocyanate on an isocyanate-equivalent basis, such as 2,6-tolylene diisocyanate, isophorone diisocyanate, hexamethylene diisocyanate, or hexamethylene diisocyanate trimer, e.g. that sold as "Desmodur N-100", [OCNC$_6$H$_{12}$N(CONHC$_6$H$_{12}$-NCO)$_2$]. Mixtures of isocyanate can be used; a particular effective mixture is one of isophorone diisocyanate and 2,4-tolylene diisocyanate in ratios of 10:1 to 1:10, e.g. 1:3. When mixtures of isocyanates are used, the component isocyanates can be reacted sequentially or the mixture as such can be used. A single fluoroaliphatic radical- and chlorine-containing alcohol can be reacted with the isocyanate, or mixtures of such alcohols can be used, or mixtures of said alcohols with alcohols free of fluoroaliphatic radicals or free of aliphatic chlorine atoms, or free of both fluoroaliphatic radicals and aliphatic chlorine atoms. It is preferred that the alcohols be free of aliphatic unsaturation, although aromatic substituents can be present provided the alcoholic hydroxyl group is bonded to an aliphatic carbon atom. Generally, the urethane should contain at least 25 wt.% carbon-bonded fluorine, in the form of fluoroaliphatic radical, and at least one aliphatic chlorine atom.

A preferred class of urethanes useful in this invention can be represented by the formula $$R_3[NHCOO-B]_o \qquad \text{VIII}$$

where $R_3$ is the isocyanate-free residue of an organic poly- isocyanate, e.g., 2,4-tolylene diisocyanate, B is the hydroxyl-free residue of an fluoroaliphatic radical-and aliphatic chlorine-containing alcohol, such as a citrate corresponding to formula VI or the hydroxyl-free residue of the above-described fluoroaliphatic radical-and chlorine-containing alcohol precursors, and o is an integer equal to the number of isocyanate groups in said isocyanate, e.g. 2 to 5.

Where mixtures of isocyanates or mixtures of alcohols are used to prepare the urethanes, $R_3$ and B will represent more than one species.

The use of the above-described fluoroaliphatic radical- and chlorine-containing esters in carpet treatment is an improvement over the carpet treatment disclosed in U.S. Pat. No. 4,043,964 (Sherman and Smith) in that said esters are used as the water-insoluble fluorinated component in the carpet treating compositions disclosed in that patent. Bearing in mind the above distinction, and others hereinafter apparent or noted, the teachings in that patent are thus incorporated herein by reference.

Thus, according to this invention, a carpet treating composition is provided comprising a liquid medium containing:

a. a water insoluble addition polymer derived from polymerizable ethylenically unsaturated monomer free of non-vinylic fluorine, said polymer having at least one major transition temperature higher than 25° C., preferably higher than 40° C., and most preferably higher than 45° C., and preferably having a solubility parameter of at least about 8.5; and b. a water-insoluble fluorinated component which is the fluoroaliphatic radical- and chlorine-containing ester described hereinbefore, said ester containing at least 25% by weight of carbon-bonded fluorine, in the form of fluoroaliphatic radical, and at least one aliphatic chlorine atom per molecule and having at least one major transition temperature higher than 25° C., preferably higher than 40° C., and most preferably higher than 45° C.

Together, the addition polymer and ester, components a and b, constitute at least 0.1 wt.% of the carpet treating composition.

Both components are characterized as being normally non-rubbery, nontacky, normally solid, water-insoluble, and preferably free of ethylenic or acetylenic unsaturation. These two components in admixture are referred to for convenience as the treating agent to distinguish from the liquid treating composition. Water-insolubility after drying of each component is required to provide durability to the normal cleaning operations such as steam cleaning. In order to be resistant to soil under high compressive load, especially particulate soil, the addition polymer and ester must have at least one major transition temperature above about 25° C., preferably above about 40° C., which is a melting point or glass transition temperature at which the composition becomes significantly softer as the temperature is raised. Transitions are characteristiclly glass temperature (Tg) or crystalline melting points (Tm), such as are usually detected by DTA (differential thermal analysis) or thermomechanical analysis (TMA). While suitable materials may have, for example, glass transitions at relatively low temperatures such as −25° C. to 0° C., the composition must have at least one major transition point above about 25° C. It is preferred that not only the addition polymer and the ester have at least one such major transition point but that the carpet treating composition comprising those materials be substantially free of non-volatile components, such as other polymers not having a major transition temperature higher than about 25° C.

The water-insoluble addition polymers useful in this invention can be prepared from a wide variety of monomers, as disclosed in said U.S. Pat. No. 4,043,964. One preferred addition polymer is an acrylate copolymer prepared by adding to a glass-lined reactor 3780 parts of water, 108 parts of a polyethoxylated stearyl ammonium chloride cationic surfactant, and 4 parts reactive cationic monomer having the formula:

$$CH_2=C(CH_3)CO_2CH_2CH(OH)CH_2N^+(CH_3)_3Cl^- \qquad \text{IX}$$

The solution is freed of oxygen by alternately evacuating and repressuring with nitrogen. 720 parts of methylmethacrylate and 720 parts of ethylmethacrylate are then added, the mixture heated to 60° C., and 14 parts of a free radical polymerization initiator (2,2'-diguanyl-2,2'-azapropane hydrochloride), dissolved in water, are added. When the reaction is initiated and the temperature begins to rise, the temperature is maintained at 85° C. while a mixture of 2380 parts methylmethacrylate, 2380 parts ethylmethacrylate, and 4200 parts of water is slowly added. Agitation at 85° C. is continued until completion, about six hours. The acrylate copolymer emulsion contains about 45% copolymer solids.

Another specific addition polymer which can be used is a flame retardant polymer prepared by charging to a stirred vessel 58 parts deionized water, 2.6 parts polyethoxylated stearyl ammonium chloride, 0.1 part cationic monomer of formula IX above, 21.5 parts methyl methacrylate, and 5.6 parts bis(2-chloroethyl)vinyl phosphonate. The polymerization vessel is evacuated and refilled with $N_2$ three times. Then 8.5 parts vinylidene chloride and a catalyst solution of 0.23 part 2,2'-azobis (2-amidinopropane)hydrochloride dissolved in 4 parts deionized water are added. In another stirred vessel an additional mixture is prepared from 56.4 parts deionized water, 5.9 parts polyethoxylated stearyl ammonium chloride, 0.2 part of cationic monomer of formula IX above, 63 parts methyl methacrylate, 5.6 parts bis(2-chloroethyl)vinyl phosphonate and 8.5 parts vinylidene chloride. This additional mixture is added to the above polymerization vessel over a 3-hour period while maintaining the temperature of the polymerization vessel at 65° C. The polymerization is permitted to continue with stirring for a further 3 hours after addition is completed.

The weight ratio of ester component to addition polymer component in the treating composition is preferably in the range of about 1:10 to 10:1, provided that the mixture of the two components contains at least about 5 percent by weight of fluorine in the form of said fluoroaliphatic radicals.

The carpet treating composition, in another aspect of this invention, usually further comprises an antistatic agent compatible with the composition, such as those antistatic agents present in currently used fluorochemical carpet treating compositions. In those currently used treating compositions, the presence of the antistatic agent adversely affects the soil resistance and stain repellancy; however, when such antistatic agents are present in the treating compositions of this invention such adverse affects are minimized or overcome.

A particularly useful antistatic agent which can be used in this invention is prepared by dissolving 350 parts of N,N-bis(hydroxyethyl) soya amine ("Ethomeen" S/12) in ethyl acetate. The solution is heated to 60° C. and 145 parts of diethyl sulfate added. Heating is continued for one hour, followed by the addition of excess water and azeotropic distillation of the ethyl acetate, resulting in 20 wt. % solids aqueous solution of the amine sulfate $$[R'N(C_2H_4OH)_2R'']^+[R''SO_4]^-$$

where R' is principally a polyunsaturated group of 12 to 18 carbon atoms and, R" is ethyl.

The weight ratio of the antistatic agent to the sum of addition polymer and ester components can vary in the range of from about 1:10 to about 1:1 and is most preferably in the range of about 1:5 to 2:3.

Carpets and rugs can be treated with the compositions of this invention by any of the customary procedures, such as by padding, spraying, roll-coating and the like. The treating agent can be applied from aqueous or non-aqueous solutions or suspensions and the antistatic agent (if any) and the fluorochemical carpet treating composition can be coapplied or applied sequentially. Alternatively, the fiber or yarn can be treated prior to conversion to carpet.

The most convenient and generally most economical procedure is to prepare a treating solution by blending appropriate quantities of the antistatic agent in the form of an aqueous solution or suspension with an aqueous suspension of the fluorochemical carpet treating agent. Conveniently, an aqueous solution comprising, for example, about 2 to 10% by weight of the antistatic agent is blended with an aqueous solution, suspension or emulsion, generally a cationic emulsion, comprising about 45% by weight carpet treating agent, and the blend further diluted with water to the desired concentration. Other conventional adjuvants compatible with the above-described components, such as softeners, wetting agents, and the like, may be added. It is also possible to achieve similar results by first coating the carpet fiber with a dispersion or solution of the addition polymer and then subsequently coating with a solution or dispersion of the ester. This two-step application imparts similar oil repellency and soil resistance to the carpet as is imparted by the co-application.

The actual concentration of treating agent in the liquid treating composition will depend on the amount of liquid to be applied during treatment. This will, in turn, depend on the construction and composition of the carpet as well as the application and drying facilities which are used. Generally a total application of treating agent equal to about 0.1 to about 5 percent of the face pile weight of the carpet is required and should be contained in an amount of water corresponding to about 3 to 150, preferably 10 to 30 percent, of the face pile dry weight.

When the carpet treatment is to be applied at the dyehouse, the most convenient method is to spray the solutions onto the carpet surface after the dyeing operation and prior to the drying oven. When treatment is to be applied as part of the backing step, the carpet can be sprayed as part of the laminating operation, to be followed by oven drying.

Following the contacting of the carpet with the carpet treating composition, the carpet is dried to remove water and solvents used in the treatment, generally with the application of heat. Preferably, heating is continued until the temperature of the carpet has exceeded 70° C. and, more preferably, exceeding 100° C. Carpets treated with the treating compositions of this invention have thereon a long-lasting, soil-and stain-resistant coating which will remain effective even after "steam cleanings" and which will survive severe abrasion Stain repellancy of carpet is evaluated in terms of oil and water repellancy. Oil repellancy is tested by preparing a mixture of 85 volume % mineral oil and 15 volume % hexadecane and placing 3 drops (about 2 inches apart) of the mixture on the carpet sample to be evaluated; if at least 2 of the drops are still visible as spherical to hemispherical after 60 seconds or more, the treatment "passes", i.e., the carpet has acceptable oil repellancy. Water repellancy is similarly tested with a mixture of 90 volume % water and 10 volume % isopropanol and if the carpet "passes" this test, the carpet has acceptable water repellancy.

Soil resistance is evaluated in general accordance with AATCC Test Method 122–1976, a walk-on test. This is a comparative test, each sample consisting of a test piece 30 by 15 cm and a control piece 30 by 15 cm. The combination is placed side by side in a heavily travelled industrial area for an exposure of about 12,000 steps. The samples are rotated periodically to insure uniform exposure and are vacuumed every 24 hours during the test and before visual evaluation.

Objects and advantages of this invention are shown in the following examples, where parts given are parts by weight.

EXAMPLE 1

In a 500 ml glass reaction flask equipped with a gas bubbler, stirrer, and dry ice-acetone condenser was placed 128 g anhydrous methanol solvent. Over a one-half hour period there was added to the flask 146 g anhydrous HCl, and then 114 g (0.2 mole) of molten

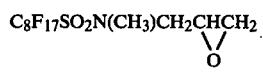

was slowly added to the flask over a twenty minute period. The contents of the flask were heated to 65° C. and stirred at 65° C. for 1.5 hours. Methanol and excess HCl were stripped from the reaction mixture at 95° C. at reduced pressure (less than 1 mm Hg) to produce a 92.7% yield (112.2 g) of a white solid product having the formula:

$$C_8F_{17}SO_2N(CH_3)CH_2CH(OH)CH_2Cl \qquad X$$

The above mode of preparation can be used to prepare similar alcohols falling within the scope of formula III from other fluoroaliphatic epoxides falling within the scope of formula II.

EXAMPLE 2

In a 1 liter, 3-neck reaction flask equipped with addition funnel, condenser, air motor stirrer, heating mantle, and thermometer was added 540 g (1 mole) $C_8F_{17}SO_2N(CH_3)C_2H_4OH$. The flask was heated to about 90° C. to melt the alcohol and a water aspirator vacuum applied to remove trace moisture. The flask contents were stirred at 90°–95° C. for 10–15 minutes. Then 5 g anhydrous SnCl$_4$ catalyst was added with a syringe to the stirred contents in the flask, and stirring at 90° C. was continued for 15 minutes. One hundred g (1.1 mole) epichlorohydrin was added slowly to the flask over a 1.5 hour period while the temperature of the contents was maintained at about 100° C. The stirring was continued for about 0.5 hour and the temperature increased to 115°-120° C. for 0.5 hour to complete the condensation reaction. The resulting product contained fluoroaliphatic radical- and chlorine-containing alcohol of the formula:

$$C_8F_{17}SO_2N(CH_3)C_2H_4[OCH_2CH(CH_2CL)]_nOH \quad \text{XI}$$

where n is an integer of 1 or 2.

The above mode of preparation can be used to prepare similar alcohols falling within the scope of formula V from other fluoroaliphatic alcohols falling within the scope of formula IV, such as those of the formulas $$C_8F_{17}SO_2N(C_2H_5)C_2H_4[OCH_2CH(CH_2Cl)]_nOH \quad \text{XII}$$

$$C_8F_{17}SO_2N(CH_3)C_4H_8[OCH_2CH(CH_2Cl)]_nOH \quad \text{XIII}$$

where n in formulas XII and XIII is 1 or 2.

EXAMPLE 3

Into a 250 ml, 2-neck reaction flask equipped with magnetic stirrer, condenser, Dean-Stark receiving trap and thermometer were added 193 g (0.3 mole) of the fluoroaliphatic radical- and chlorine-containing alcohol of formula XI, 21 g (0.1 mole) citric acid monohydrate, 30 g toluene (as azeotropic solvent), and 0.04 g p-toluene sulfonic acid (as catalyst). The contents of the flask were slowly heated to 50° C., 0.25 g concentrated $H_2SO_4$ was added with stirring and the mixture heated to reflux (about 120° C.). After 6.2 g water collected in the Dean-Stark trap, the resulting product was allowed to cool, the product being a toluene solution of the citrate of the formula:

$$[C_8F_{17}SO_2N(CH_3)C_2H_4O(C_3H_5ClO)_nOC]_3C_3H_4OH \quad \text{XIV}$$

where n is 1 or 2.

One half of the toluene solution was mixed with 55 g methyl isobutyl ketone and 2.6 g polyoxyethylene sorbitan monooleate ("TWEEN" 80), the mixture heated to 75°-80° C. and added to 163 g deonized water containing 13 g of a 20% water-acetone solution of a cationic fluoroaliphatic surfactant, $C_8F_{17}SO_2NHC_3H_6N^+(CH_3)_3Cl^-$, the resulting emulsion of the citrate having 30% active solids.

Following the above procedure, other similar polycarboxylic acid esters can be prepared such as the citrate of the formula:

$$[C_8F_{17}SO_2N(C_2H_5)C_2H_4O(C_3H_5ClO)_nOC]_3C_3H_4OH \quad \text{XV}$$

where n is 1 or 2.

EXAMPLE 4

To one mole of the fluoroaliphatic chloroisopropanol of formula X, as a 62.5% solution in methyl isobutyl ketone solvent was added 87 parts (0.5 mole) 2,4-tolylene diisocyanate and the mixture allowed to react at 85° C. for 1.5 hour. There was added then very slowly 0.32 g of dibutyltin dilaurate as the exothermic reaction permitted. The mixture was maintained at 80°-85° C. until samples examined by infrared analysis showed no free isocyanate. The product was a solution of fluoroaliphatic radical- and chlorine- containing urethane of the formula:

$$[C_8F_{17}SO_2N(CH_3)CH_2CH(CH_2Cl)OOCNH]_2C_6H_3CH_3 \quad \text{XVI}$$

An emulsion (40% solids) was prepared by adding to the mixture 675 parts of water containing 17.25 parts of fluoroaliphatic surfactant, $C_8F_{17}SO_2NHC_3H_6N^+(CH_3)_3Cl^-$, and 17.25 parts of polyoxyethylene sorbitan monooleate ("Tween" 80) and then putting the total dispersion through a Manton Gaulin homogenizer at 2500 psi and 75°-85° C.

The above procedure can be followed to prepare a wide variety of urethanes of fluoroaliphatic radical- and chlorine-containing alcohols, such urethanes following within the scope of formula VIII and exemplified by the following table for purposes of brevity:

| Formula no. for urethane $R_3[NHCOO-B]_o$ | Precursor Reactants for Urethane | | |
|---|---|---|---|
| | Isocyanate $R_3(NCO)_o$ | Alcohol BOH | o |
| XVII | 2,4-tolylene diisocyanate | Formula XV | 2 |
| XVIII | 2,4-tolylene diisocyanate | Formula XI | 2 |
| XIX | 2,4-tolylene diisocyanate | Formula XIV | 2 |
| XX | Aliphatic polyisocyanate* | Formula XIV | 2.5 |
| XXI | 2,4-tolylene diisocyanate | Formula XIII | 2 |
| XXII** | 2,4-tolylene diisocyanate | Formula XI plus $C_8F_{17}SO_2N(CH_3)C_4H_8OH$ | 2 |
| XXIII | 2,4-tolylene diisocyanate | Formula X | 2 |

*This isocyanate was $OCNC_6H_{12}N(CONHC_6H_{12}NCO)_2$ sold as "Desmodur" N100 polyisocyanate
**The 2 alcohols used to prepare this urethane were in a 1:1 mole ratio.

EXAMPLE 5

One-half mole (320 g) of the fluoroaliphatic radical- and chlorine-containing alcohol of formula XI was added to 500-ml, 3-neck reaction flask equipped with air motor, condenser, thermometer, heating mantle and addition funnel. Sufficient anhydrous ethyl acetate (107 g) was added to the flask to provide a 75% solution, and then 13.9 g (1/16 mole) isophorone diisocyanate was added. The contents of the flask were heated slowly until clear (at about 50° C.). The contents were allowed to react at reflux (about 80° C.) for 2 hours. After cooling to 55° C., 32.7 g (3/16 mole) of 2,4-tolylene diisocyanate was added slowly over a 10-15 minutes period. The temperature was raised to reflux (about 90° C.) and the contents allowed to react at 80° C. until samples examined by infrared analysis showed no free isocyanate, about 2 hours. The product was a 77% ethyl acetate solution of a fluoroaliphatic radical-and chlorine-containing polyurethane, of the formula:

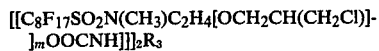   XXIV where $R_3$ is a mixture of

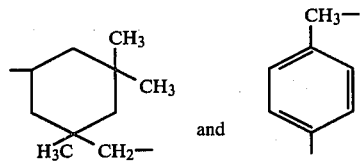

The 77% ethyl acetate solution was converted to a carpet treating composition in the following manner.

To 100 parts of the ethyl acetate solution were added 96 parts water containing 3 parts of the fluoroaliphatic surfactant used in Example 4 and 1 part of "Tween" 80. The resulting mixture was passed through the homogenizer at 2500 psi and 75°–85° C. The resulting emulsion was heated at about 72° C. to remove substantially all of the ethyl acetate by azeotropic distillation, the remaining solution comprising a 45% emulsion of the urethane. One part of the solvent-less emulsion was blended with two parts of the acrylate copolymer emulsion prepared as described hereinbefore to form the carpet treating composition.

Mixtures of alcohols can be used in the above procedure to prepare other urethanes; for example, instead of 0.5 mole of the alcohol of formula XI, 0.35 mole of such alcohol in admixture with 0.15 mole of the alcohol $C_8F_{17}SO_2N(CH_3)C_2H_4OH$ was used to form the urethane of the formula:

$R_3[(NHCOO-B)]_o$   XXV where $R_3$ is a 1:3 mixture of the same isophorone diisocyanate and tolylene diisocyanate residues, respectively, shown above for formula XXIV, and B is a 70:30 mixture of

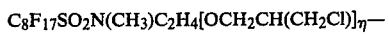

and

EXAMPLE 6

Various fluorochemical carpet treating compositions of this invention were applied to samples of a variety of carpets which had proven difficult to treat with a conventional fluorochemical treating composition, and the oil and water repellancy of the so-treated samples were determined. These carpets were composed of nylon, acrylic, polypropylene and polyester fibers, with cut pile and loop pile construction, and with face pile weights varying from 16 to 50 ounces per square yard. Each of the treating compositions of this invention were aqueous suspensions, prepared as described in the examples hereinbefore and containing, unless otherwise noted, 0.7 wt. % of a fluoroaliphatic radical- and chlorine-containing ester of this invention, 1.4 wt. % of an addition polymer and, where used, 0.5 wt. % of an antistatic agent. Unless otherwise noted, the addition polymer used in the treating composition was the preferred acrylate copolymer, described hereinbefore. The antistatic agent used was the amine sulfate described hereinbefore.

The carpet samples were sprayed with the treating composition to deposit thereon 13 to 17 wt % of the composition, based on the weight of the face pile, the sprayed carpet dried at 70° C. for about 2 hours and then heated to 100° C. or 130° C., as indicated below, for about 10 minutes. The so-treated carpet samples were then tested for oil and water repellancy using the test methods described hereinbefore. For purposes of comparison, carpet samples were also treated with a control carpet treating composition which had the same formulation except that the fluoroaliphatic radical- containing component used was a chlorine-free urethane prepared according to Example IX of U.S. Pat. No. 3,916,053 (Sherman et al).

The results of the above treatments are summarized in the following table.

| | | | Repellancy Results | | | |
| | | | Without antistatic agent | | With antistatic agent | |
| Test No. | Ester component in treating composition | Heating temp., °C. | Oil repellancy | Water repellancy | Oil repellancy | Water repellancy |
| --- | --- | --- | --- | --- | --- | --- |
| 1. | Chlorine-free urethane | 100 | F | F | F | F |
| | | 130 | P | P | P | P |
| 2. | Citrate of formula XV | 100 | P | P | P | P |
| 3. | Citrate of formula XIV | 100 | P | P | P | P |
| | | 130 | P | P | P | P |
| 4. | Urethane of formula XXI | 100 | P | P | P | P |
| 5. | Urethane of formula XXII | 100 | P | P | P | P |
| 6. | Urethane of formula XVIII | 100 | P | P | P | P |
| | | 130 | P | P | P | P |
| 7*. | Urethane of formula XVIII | 100 | P | P | P | P |
| 8. | Urethane of formula XVI | 100 | MP** | MP | MP | MP |
| 9. | Urethane of formula XXIV | 100 | P | P | P | P |
| 10. | Urethane of formula XVII | 100 | P | P | P | P |
| 11. | Urethane of formula XIX | 100 | P | P | P | P |
| 12. | Urethane of formula XX | 100 | P | P | P | P |
| | | 130 | P | P | P | P |

*The addition polymer used in the treating composition of this test was the flame retardant addition polymer.
**"MP" means the treating agent resulted in minimally passing the repellancy test.

Additionally, several of the carpet samples treated, respectively, with the control carpet treating composition (including antistat) and with those treating compositions of this invention used in Test Nos. 3, 10 and 12 were subjected to the aforedescribed walk-on test. The carpet samples treated with treating compositions of this invention showed about the same resistance to dry soil as the control composition.

EXAMPLE 7

Carpets encountered from a mill have a variety of contaminants at variable concentrations; evaluation of fluorochemical treating agents on such carpet is difficult and reproducible results are seldom obtained. Thus, a method was developed for obtaining reproducibly contaminated carpet samples for evaluation of treating agents.

The carpet used in this method is a 32 ounce per square yard, tufted, unlaminated, cut pile nylon carpet, beck-dyed light brown. A 2000-g portion of such carpet, as received from the mill, is scoured in an aqueous solution (heated to 70° C.) comprising 80 liters of water containing 40 g tetrasodium pyrophosphate and 40 g polyethoxylated nonyl phenol ("Tanapon" X-70), using a home washing machine with a 15 minute wash cycle. After the wash cycle, the carpet is rinsed in about 45° C. water and tumble dried at 70° C.

To "contaminate" the thus-scoured carpet, it is passed through a bath of solution prepared from 78 parts distilled water, 20 parts polyoxypropylene glycol (2000 molecular weight), and 2 parts polyethoxylated nonyl phenol, then passed through a squeeze roll adjusted to 30 wt. % wet pick-up and dried in a circulating air oven at 70° C.

The contaminated carpet is treated with the fluorochemical treating composition by an airless spray depositing 0.3 wt. % solids (which corresponds to about a 15 wt. % wet pick-up). Treated samples of the carpet are then dried at 70° C. in a circulating air oven, followed by heating at 100° C. for 10 minutes. Samples are tested for oil and water repellancy after at least 24 hours standing at 20° C. and 50% relative humidity.

Carpet contaminated and treated in the above-described manner with the fluorochemical treating composition containing as the fluoroaliphatic radical- and chlorine-containing ester the urethane of formula XXIV described in Example 6, with and without the antistatic agent, was tested for oil and water repellancy in the manner described hereinbefore. The results of testing are set forth in the table below together, for purposes of comparison, with the results obtained on contaminated carpet treated with the control containing the chlorine-free urethane.

| | Repellancy Results | | | |
| | Without antistatic agent | | With antistatic agent | |
| Test No. | Ester component in treating composition | Oil repellancy | Water repellancy | Oil repellancy | Water repellancy |
|---|---|---|---|---|---|
| 1. | Chlorine-free urethane | F | F | F | F |
| 2. | Urethane of formula XXIV | P | P | P | P |

Treatment of carpet scoured as described above, but not contaminated, resulted in satisfactory repellancy with either of said treating agents.

EXAMPLE 8

In a glass flask fitted with addition funnel, condenser, stirrer, heating mantle, and thermometer were placed 670 parts (one mol) of an alcohol of formula XI (Example 2), 73 parts (0.5 mol) adipic acid, and 480 parts toluene. The contents of the flask were heated slowly, with stirring, to about 80° C. and then 2.2 parts concentrated sulfuric acid was added. The reaction mixture was heated to reflux and water removed by a modified Dean-Stark trap. After 16 hours of reflux, the reaction was completed; toluene was removed by distillation at atmospheric pressure, leaving 691 parts of residual product, a light tan solid melting at 64°–82° C. Elemental and spectroscopic analysis verified the identity of the product as an adipate ester of the formula:

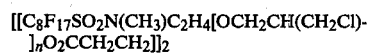

$$[[C_8F_{17}SO_2N(CH_3)C_2H_4[OCH_2CH(CH_2Cl)-]_nO_2CCH_2CH_2]]_2 \quad \text{XVII}$$

A latex suitable as a composition for treating contaminated carpet was prepared by combining the following components:

| No. | Component | Amount |
|---|---|---|
| 1. | Adipate ester of Formula XVII | 100 parts |
| 2. | Ethyl acetate | 60 parts |
| 3. | "TWEEN" 80 | 3.75 parts |
| 4. | $C_8F_{17}SO_2NHC_3H_6N^+(CH_3)_3Cl^-$ | 1.25 parts |
| 5. | Deionized water | 140 parts |

The first three components (1–3) of the above formulation were placed in glass flask and heated with stirring to about 75° C. to form a first solution. A second solution of the last two components (4,5) was made, heated to 75° C., combined with the first solution and the mixture passed through a mechanical homogenizer to form a stable latex containing about 34 weight percent solids. Equally satisfactory results were obtained when all five components were combined, heated, and homogenized.

A carpet treating concentrate was prepared by combining the above latex with the above described preferred acrylate addition copolymer emulsion (48 weight percent copolymer solids) to provide a latex (43 weight percent solids, containing 15 weight percent fluorine) with a ratio of fluoroaliphatic polymer solids: addition polymer solids of 1:2. The concentrate was diluted with water to about 2 weight percent solids and the diluted concentrate then sprayed on test carpets in the manner described in Example 6.

Two types of test carpet were used. Carpet "A" was a space-dyed, blue, loop-pile nylon carpet contaminated with silicone lubricating oils with fiber weight of 14 ounces per square yard, and carpet "B" was a beck-dyed, gold, cut-pile nylon splush carpet relatively free of contaminants and weighing 50 ounces per square yard. The diluted concentrate was applied to a level of 0.24 weight percent solids based on the weight of the carpet face-pile fiber in the case of carpet B and 0.36 percent on carpet A. The treated carpet samples were dried in a circulating air oven for about 20 minutes at 70° C. and then carpet A cured for about 10 minutes at 100° C. and carpet B at 130° C.

For purposes of comparison, other samples of such test carpet were similarly treated with the control composition described in Example 6.

The results of the above treatments are summarized in the following table.

| Carpet | Treating Compositions | Repellancy Results | |
|---|---|---|---|
| | | Oil Repellancy | Water Repellancy |
| A | Composition containing adipate | P | P |
| A | Control | F | P |
| B | Composition containing adipate | P | P |
| B | Control | P | P |

Since some carpet mills use water which is comparatively hard and may use application equipment in the practice of this invention which may subject the aqueous treating suspensions of this invention to severe mechanical stress and, thus, coagulation of such suspensions may be encountered. Thus, it may be desirable to add to such treating compositions a stabilizer or anticoagulant to prevent or minimize such coagulation. For example, a more stable aqueous suspension treating composition was prepared by adding to the adipate-containing concentrate described above a small amount, for example 5-20 percent by weight of the adipate solids, of a hydrophilic polymer such as described in U.S. Pat. No. 3,574,791, particularly that described in Example 19 of that patent; the stabilized treating composition had about the same effectiveness in improving stain repellancy and soil resistance as did the treating compositions without stabilizer.

EXAMPLE 9

A maleic ester of the alcohol of formula XI (Example 2) was prepared by using the esterification method of Example 8 except that a molar equivalent of maleic acid was used in place of the adipic acid, other reactants and conditions being the same. The resulting maleate-containing concentrate was then converted to a carpet treating composition using the technique described in Example 8 and applied to two test carpets. One of the test carpets was carpet B of Example 7 and the other, carpet C, was a contaminated, yarn-dyed, brown, cut-pile nylon carpet having 28 ounces per square yard of fiber. For purposes of comparison, carpet samples were also treated with the same control treating composition described in Example 6.

The results of the above treatments are summarized in the following table.

| Carpet | Treating Composition | Repellancy Results | |
|---|---|---|---|
| | | Oil Repellancy | Water Repellancy |
| B | Composition containing maleate | P | P |
| B | Control | P | P |
| C | Composition containing maleate | P | P |
| C | Control | F | P |

In a similar manner, other fluoroaliphatic radical and chlorine-containing esters were prepared from dichloromaleic anhydride, dibromomaleic anhydride, phthalic anhydride, malonic acid, succinic acid, hydroxy succinic acid, and the like in place of maleic acid; these other esters showed similar properties.

EXAMPLE 10

A carpet treating composition in the form of methyl isobutyl ketone solution was prepared containing 0.17 percent by weight of the adipate ester of Example 8 and 0.34 percent by weight of said preferred addition polymer. A control treating composition was prepared in the form of a methyl isobutyl ketone solution containing 0.17 percent by weight of bis(N-methyl perfluorooctane sulfonamidoethyl)adipate and 0.34 percent by weight of said addition polymer. The above treating compositions were sprayed on samples of said test carpet A to deposit in each case 0.33 weight percent solids on fiber, and the treated samples dried for 20 minutes at 70° C. and cured for 10 minutes at 100° C.

The results of the above treatments are summarized in the following table.

| Carpet | Treating Composition | Repellancy Results | |
|---|---|---|---|
| | | Oil Repellancy | Water Repellancy |
| A | Composition containing adipate | P | P |
| A | Control | F | F |

Other samples of the above described treated carpets were subjected to aforedescribed walk-on test. The resistance to dry soil of the carpet treated with the above described adipate-containing solution was significantly better than the carpet treated with the said control treating composition.

Various modification and alterations of this invention will become apparent to those skilled in the art without departing from the scope and spirit of this invention.

What is claimed is:

1. An alcohol having the formula $$R_f-Q-A-OH$$

where $R_f$ is a fluoroaliphatic, saturated, monovalent radical having at least three fully fluorinated carbon atoms and not more than 20 carbon atoms, said alcohol having more than 25 weight % carbon-bonded fluorine in the form of said fluoroaliphatic radical, Q is selected from the group consisting of —CO—, —CONR—, —SO$_2$NR—, —SO$_2$—, C$_n$H$_{2n}$—, —C$_6$H$_4$—, —C$_6$H$_3$Cl—, —OC$_2$H$_4$—, or combinations thereof, where R is H or lower alkyl containing 1 to 6 carbon atoms, and n is 1 to 20, and A is a divalent organic moiety having 2 to 30 carbon atoms, containing at least one aliphatic chlorine atom, and free of hydroxyl-reactive substituents, said alcohol upon reaction with a mono- or polycarboxylic acid forming the corresponding ester which in combination with water-insoluble addition polymer derived from polymerizable ethylenically unsaturated monomer free of nonvinylic fluorine forms a composition suitable for the treatment of carpet to render it durably soil resistant and stain repellant, said ester containing at least 25 percent by weight of carbon-bonded fluorine, in the form of said fluoroaliphatic radical, and having at least one major transition temperature higher than about 25° C., said polymer having at least one major transition temperature higher than about 25° C.

2. An alcohol having the formula $$R_f(Q)_mCH(OH)CHRCl$$

where

R is hydrogen or lower alkyl, $R_f$ is a fluoroaliphatic, saturated, monovalent radical having at least three fully fluorinated carbon atoms and not more than 20 carbon atoms, said alcohol having more than 25 weight % carbon-bonded fluorine in the form of said fluoroaliphatic radical, Q is selected from the group consisting of —CO—, —CONR—, —SO$_2$NR—, —SO$_2$, —C$_n$H$_{2n}$—, —C$_6$H$_4$—, —C$_6$H$_3$Cl—, OC$_2$H$_4$—, or combinations thereof, where R is H or lower alkyl containing 1–6 carbons, m is 1.

3. An alcohol having the formula

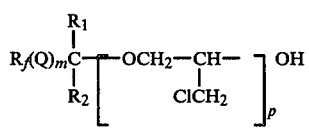

where
- R$_1$ is hydrogen or lower alkyl,
- R$_2$ is hydrogen, lower alkyl, or aryl,
- R$_f$ is a fluoroaliphatic, saturated, monovalent radical having at least three fully fluorinated carbon atoms and not more than 20 carbon atoms, said alcohol having more than 25 weight % carbon-bonded fluorine in the form of said fluoroaliphatic radical,
- Q is selected from the group consisting of —CO—, —CONR—, —SO$_2$NR—, —SO$_2$—, —C$_n$H$_{2n}$—, —C$_6$H$_4$—, —C$_6$H$_3$Cl—, OC$_2$H$_4$—, or combinations thereof where R is H or lower alkyl containing 1–6 carbons,
- m is 1, and
- p is an integer of 1 to 5.

* * * * *

UNITED STATES PATENT AND TRADEMARK OFFICE
CERTIFICATE OF CORRECTION

PATENT NO. : 4,468,527
DATED : August 28, 1984
INVENTOR(S) : Kalyanji U. Patel

It is certified that error appears in the above-identified patent and that said Letters Patent is hereby corrected as shown below:

Col. 2, line 59, "$-C_6H_2Cl-$" should read -- $-C_6H_3Cl-$ -- .

Col. 3, line 53, the $R_1$ portion of the formula should
"$\underset{R_2}{\overset{R_1}{C}}$"

read $-\underset{R_2}{\overset{R_1}{\underset{|}{\overset{|}{C}}}}-$ .

Col. 16, line 40, "$C_nH_{2n}-$" should read -- $-C_nH_{2n}-$ -- .

Col. 17, line 4, "$-SO_2$" should read -- $-SO_2-$ -- .

Signed and Sealed this

Twenty-third Day of April 1985

[SEAL]

Attest:

DONALD J. QUIGG

Attesting Officer    Acting Commissioner of Patents and Trademarks